(12) United States Patent
Richmond et al.

(10) Patent No.: US 7,442,212 B2
(45) Date of Patent: Oct. 28, 2008

(54) DECODING ALGORITHM FOR NEURONAL RESPONSES

(75) Inventors: Barry J. Richmond, Bethesda, MD (US); Matthew Wiener, Westfield, NJ (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 524 days.

(21) Appl. No.: 10/250,543

(22) PCT Filed: Jan. 11, 2002

(86) PCT No.: PCT/US02/00942

§ 371 (c)(1),
(2), (4) Date: Apr. 26, 2004

(87) PCT Pub. No.: WO02/054951

PCT Pub. Date: Jul. 18, 2002

(65) Prior Publication Data

US 2004/0204769 A1    Oct. 14, 2004

Related U.S. Application Data

(60) Provisional application No. 60/261,494, filed on Jan. 12, 2001.

(51) Int. Cl.
*A61F 2/70* (2006.01)
(52) U.S. Cl. ...................................... 623/25
(58) Field of Classification Search ............ 623/24, 623/25; 600/545–547
See application file for complete search history.

(56) References Cited

U.S. PATENT DOCUMENTS

| | | | |
|---|---|---|---|
| 3,883,900 A | 5/1975 | Jerard et al. | |
| 4,030,141 A | 6/1977 | Graupe | |
| 4,611,284 A | 9/1986 | Mcgill et al. | |
| 5,037,376 A | 8/1991 | Richmond et al. | |
| 6,163,725 A | 12/2000 | Peckham et al. | |
| 2003/0097159 A1* | 5/2003 | Schiff et al. ................... | 607/45 |

FOREIGN PATENT DOCUMENTS

| | | |
|---|---|---|
| EP | 0 357 212 | 3/1990 |
| WO | 00/09008 | 2/2000 |
| WO | 01/13778 | 3/2001 |
| WO | 01/43635 | 6/2001 |

OTHER PUBLICATIONS

Erfanian, et al., "Using Evoked EMG as a Synthetic Force Sensor of Isometric Electrically stimulated Muscle", IEEE Transactions on Biomedical Engineering, vol. 45, No. 2, Feb. 1998, pp. 188-202.

Abbott L.F., "Decoding Neuronal Firing and Modeling Neural Networks" Quarterly Reviews of Biophysics, ISSN: 0033-5835, 'Online! Aug. 1994, pp. 291-331.

Dayan, et al., "Chapter 1: Neural Encoding I: Firing Rates and Spike Statistics, Theoretical Neuroscience", 'Online!, Oct. 2000, pp. 1-42.

Heller, et al., "Information Flow and temporal coding in Primate Pattern Vision", Journal of Computational Neuroscience, vol. 2, No. 3, 175-193, Sep. 1995.

Oram, et al., Stochastic Nature of Precisely Timed Spike Patterns in Visual System Neuronal Responses, Journal of Neurophysiology, vol. 81, No. 6, 3021-3033, Jun. 1999.

Prut, et al., "Spatiotemporal Structure of Cortical Activity: Properties and Behavioral Relevance", Journal of Neurophysiology, vol. 79, No. 6, 2857-2874, Jun. 1998.

Kwatra, et al., "A neuro-Mimetic Dynamic Scheduling Algorithm for Control: Analysis and Applications", Neural Computation, vol. 9, No. 3, 479-502, 1997.

Abeles, et al., "Detecting Spatiotemporal Firing Patterns Among Simultaneously Recorded Single Neurons", Journal of Neurophysiology, vol. 60, 909-924, 1988.

Ihaka, et al., "R: A Language for Data Analysis and Graphics", Journal of Computational and Graphical Statistics, vol. 5, No. 3, 299-314, Sep. 1996.

Richmond, et al., "Temporal Encloding of Two-Dimensional Patterns by Single units in Primate Inferior Temporal Cortex. II. Quantification of Response Waveform", Journal of Neurophysiology, vol. 57, No. 1, 147-161, Jan. 1987.

Laubach, et al., "Cortical ensemble activity increasingly predicts behavior outcomes during learning of a motor task", Nature, vol. 405, 567-571, Jun. 2000.

Oram, et al., "Stochastic Nature of Precisely Timed Spike Patterns in Visual System Neuronal Responses", J. Neurophysiol., vol. 81, 3021-3033, 1999.

Wiener, et al., "Using Response Models to Estimate Channel Capacity for Neuronal Classification of Stationary Visual Stimuli Using Temporal Coding", J. Neurophysiol., vol. 82, 2861-2875, 1999.

Gershon, et al., "Coding Strategies in Monkey VI and Inferior Temporal Cortices", J. Neurophysiol., vol. 79, 1135-1144, 1998.

Wiener, et al., Using response models to study coding strategies in monkey visual cortex, BioSystems, vol. 48, 279-286, 1998.

Richomd, et al., "Repsonse Features Determining Spike Times", Neural Plasticity, vol. 6, No. 4, 133-145, 1999.

Craven, et al., "Smoothing Noisy data with Spline Functions", Numerische Mathematik, vol. 31,377-403, 1979.

Chapin, et al., "Real-time control of robot arm using simultaneously recorded neurons in the motor cortex", Nature Neuroscience, vol. 2, No. 7, 664-670, Jul. 1999.

Wessberg, et al., "Real-time prediction of hand trajectory by ensembles of cortical neurons in primates", Nature, vol. 408, 361-365, Nov. 2000.

Erfanian, et al., "Using Evoked EMG as Synthetic Force Sensor of Isometric Electrically Stimulated Muscle", Transactions on Biomedical Engineering, vol. 45, No. 2, 188-202, Feb. 1998.

Abbott, L.F., "Decoding Neuronal Firing and Modeling Neural Networks", Quart. Rev. Biophyys., vol. 27, 291-331, 1994.

Dayan, et al., "Chapter I: Neural Enclonding I: Firing Rates and Spike Statistics", Theoretical Neuroscience, 1-42, Oct. 11, 2000.

* cited by examiner

*Primary Examiner*—Bruce E. Snow
(74) *Attorney, Agent, or Firm*—Katherine M. Kowalchyk; Merchant & Gould P.C.

(57) ABSTRACT

A device and method for decoding neuronal responses wherein sequences of potentials from neurons are monitored while specific motor tasks are carried out, and these sequences are characterized using order statistics and subsequently the order statistics are used to decode action potentials representing unidentified motor tasks to determine the desired motor task. The method of the invention comprises the steps of monitoring action potentials caused by a motor task being requested by the brain, calculating a spike density function and order tasks for each distinct motor task, to relate action potentials to their specific motor task. The invention also offers methods of formulating instructions for a prosthetic device. This method comprises the steps of learning the neuronal responses of distinct motor tasks by monitoring action potentials caused by a motor task being requested by the brain, calculating a cumulative density function for each distinct motor task, and using order statistics to relate action potentials to their respective motor tasks; monitoring action potentials from at least one neuron of said user wherein the action potentials are caused by the request for an unknown motor task; using said learned neuronal responses to determine which motor task is being requested by the monitored neuron; and formulating instructions on how to carry out the requested motor task. The device of the invention comprises a prosthetic limb, a device capable of making said prosthetic limb carry out motor tasks, a device capable of recording action potentials from neurons, and a device containing instructions for monitoring neurons, calculating cumulative density functions, utilizing order statistics, and determining instructions for various motor tasks.

8 Claims, 11 Drawing Sheets

DECODING ALGORITHM FOR NEURONAL RESPONSES

This application is a 371 of PCT/US02/00942, filed Jan. 11, 2002, which claims benefit of U.S. provisional application 60/261,494 filed Jan. 12, 2001.

This application is being filed as a PCT international patent application in the name of The Government of the United States of America, as Represented by the Secretary, Department of Health and Human Services (applicant for all designations except the U.S.), and in the names of Barry J. Richmond and Matthew Wiener, both U.S. citizens and residents (applicants for the U.S. designation only), on 11 Jan. 2002, designating all countries.

FIELD OF THE INVENTION

The invention relates to the decoding of neuronal signals. More specifically the invention relates to methods of decoding neuronal signals so that the decoded neuronal signals can be translated into instructions for mechanical action of a prosthesis.

BACKGROUND OF THE INVENTION

The development of prosthetic devices is a complex technological field. Prosthetic devices must be engineered to be both aesthetically pleasing and functional. Functionality not only requires that the prosthetic device be mechanically capable of accomplishing the required movements, but there must also be a system by which the user of the prosthetic device can "control" the device. User "control" of prosthetic devices remains an area where advances are still necessary.

At first, simple prosthetic devices were controlled by a different, non-impaired part of the body. For example, using shoulder or stomach movements to initiate elbow bending, wrist movements or grasping of an artificial arm. Preferred methods of controlling prosthetic devices are commonly referred to as "EMG" or electromyogram actuated systems. An EMG-actuated system controls the prosthesis by direct synchronous control over or monitoring of the muscles that were originally responsible for the movement, and near simultaneous control over the prosthesis by the user's brain stimulating the same muscle system that formerly controlled the limb. Previously implemented EMG-actuated systems, while progressing rapidly, have met with limited success and suffer from significant drawbacks.

A recently reported EMG-actuated system, J. Wessberg et al., Real-time prediction of hand trajectory by ensembles of cortical neurons in primates, *Nature* 408: 361-365, 2000, has overcome some drawbacks normally found in these methods. This method began by recording neuronal impulses of primates generated by a specific type of motor skill. Then, the neuronal impulses were averaged and summed by following a population vector approach. The neuronal impulses associated with a specific mechanical action were then estimated.

This method, although a considerable advance, has two significant drawbacks. First, the method requires a large amount of data. Neuronal impulses of the two subjects were recorded for 12 and 24 months respectively for the prediction of two motor tasks. Such a method would require an inordinate amount of "training" time in order for a patient to teach their prosthesis a relatively small number of motor skills. Second, although the method requires a substantial amount of data collection time, the estimation of the ultimate motor task that corresponds to the specific neuronal impulses is statistically not optimal. Unacceptable ambiguity in the corresponding motor task would result and perhaps even an inability to accomplish more detailed motor tasks.

Therefore, there still exists a need for a method of controlling a prosthetic device through monitoring of neuronal impulses associated with motor tasks that can "learn" a reasonable amount of motor skills in a reasonable time and still offer the user of the prosthesis access to more detailed motor skills.

SUMMARY OF THE INVENTION

The invention provides a method of decoding neuronal impulses to determine the specific corresponding motor task.

The invention also offers a method of creating instructions for a prosthetic device by monitoring neuronal impulses associated with a specific motor task, corresponding specific neuronal impulses to specific motor tasks, formulating the desired motor task by monitoring neuronal impulses from the wearer of the prosthetic device, and relaying to the mechanical motors of the prosthesis the desired motor task.

The invention also offers a device preferably comprising a neuronal probe, a computer processor and an electronic media storage device containing algorithms to decode the neuronal signals and convert them to instructions for mechanical action, and a prosthetic device.

BRIEF DESCRIPTION OF THE DRAWINGS

FIGS. 4A, C, E, and G depict numerous spike trains, elicited by four different stimuli, recorded from a single neuron. The x axis shows time from stimulus onset in milliseconds and the y axis shows separate trials.

FIGS. 4B, D, F, and H depict the spike density functions for the spike trains depicted in FIGS. 4A, C, E, and G respectively. The gray histograms sum the data of all the trials and the curves show the spike density functions which are smoothed versions of the histograms.

DETAILED DESCRIPTION OF THE PREFERRED EMBODIMENTS

Decoding neuronal responses is difficult in part because it has not previously been clear which parts of a response carry relevant information and which parts do not. It has recently been shown that all of the information carried by a single neuron is available from only two characteristics of the neuronal signal, the number of impulses and a smoothed version of the probability of observing an impulse at particular times after onset of the stimulus. As used herein, the word "stimulus" refers to a desired motor task, such as for example moving a prosthesis or a prosthetic limb in a particular direction.

The recognition of the two important aspects of a neuronal signal allows more efficient monitoring thereof. Because these two characteristics of the neuronal signal contain the relevant information of the spike train, spike trains can be described using a well established branch of statistics, order statistics. Order statistics, in this context, allows estimation of the probability with which the next impulse in a spike train can be expected to occur at different times under a variety of conditions. Thus the arrival or absence of an impulse at each successive instant in time can be used to update the current estimate of which condition generated the spike train.

This type of continuous updating of the estimate of the specific spike train can be used as a part of an algorithm to decode the spike trains. This algorithm can function with an arbitrarily large number of neurons, which would allow an efficient identification of detailed motor tasks. The number of neurons that can be monitored and decoded in the algorithm is limited only by computational resources and technology. A compact, rather inexpensive device that could simultaneously monitor and decode on the order of hundreds of neurons could easily be constructed given current technology.

Through the use of an algorithm or a decoding device of the invention, a prosthetic device can be controlled by neuronal signals in real time after collecting a modest amount of data to calibrate the device. The data is collected by means of technology that is well known in the art. From the collected data, one can quickly and accurately estimate the specificity with which the prosthetic device can be controlled. Although there is a great deal of research concentrating on developing a decoder for neuronal signals, this method has the significant advantage of being very efficient. This allows collection of a limited amount of data for calibration, which translates into comparably less time spent on data collection.

The invention is based on the practice of describing spike trains by the number of impulses in the spike train and a smoothed version of the average number of impulses over time that make up the spike train. Order statistics can then be used to analyze spike trains as they are recorded.

1. Spike Trains

The neuron is the basic operating unit of the nervous system. The function of a neuron is to transmit information from one part of the body to another; that is either to transmit information about a stimulus to other neurons or to cause a motor task to be performed based upon a stimulus. As noted above, the terms "stimulus" and "motor task" are used interchangeably where the discussion focuses on the cause of a neuronal signal.

The information regarding the stimulus is transmitted in the form of an electrochemical signal called a neural impulse. There are two types of neural impulses graded potentials and action potentials. Action potentials are brief reversals in the polarity of the dendrites, soma, and axon of the cell. Graded potentials are electric potentials that cause the action potentials to fire. The action potential functions to transmit the information from the neuron to some other portion of the body. This other portion can be either another nerve cell or a muscle cell. When the other portion of the body is a muscle cell, the purpose of transmitting the information is to carry out a movement of the muscle. Therefore, such action potentials control muscular movement in the human body.

When the brain wants a muscle to move, neurons fire action potentials to the specific muscles that cause the movement. Specific motor tasks require control by a number of different neurons. A specific motor task will require a number of action potentials to be fired. The firing of action potentials occurs over a period of milliseconds. A trace of an action potential fired over time is called a spike train. A graphical depiction of a number of spike trains can be seen in FIG. 1A.

Both the distribution of spike counts and the smoothed average firing rate profile over time of responses elicited by a stimulus influence spike timing in spike trains. A model that preserves both of these properties of spike trains but otherwise chooses spike times stochastically can correctly predict aspects of millisecond-level spike timing.

Figure 1A:
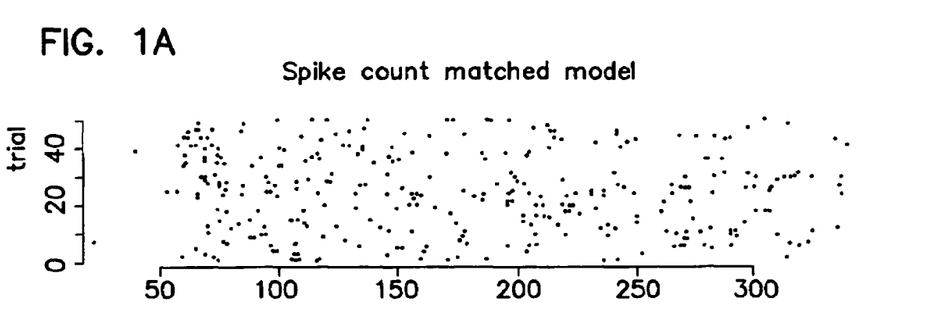
FIG. 1A is a graph representing action potentials recorded as a function of time (msec), also referred to as a spike train, for a single neuron recorded a number of different times (each horizontal line represents one recordation of the neuron).
Figure 1B:
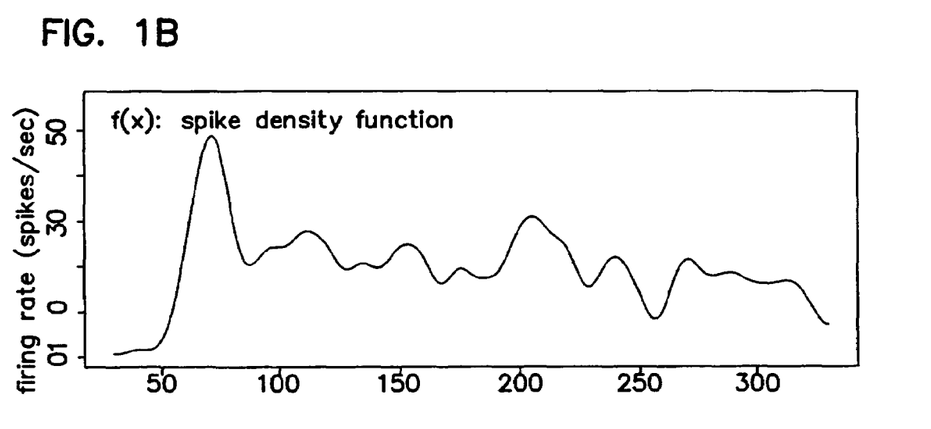
FIG. 1B is a graph representing the summation of the spike trains in FIG. 1A, also referred to as the spike density function $f(x)$.
Figure 1C:
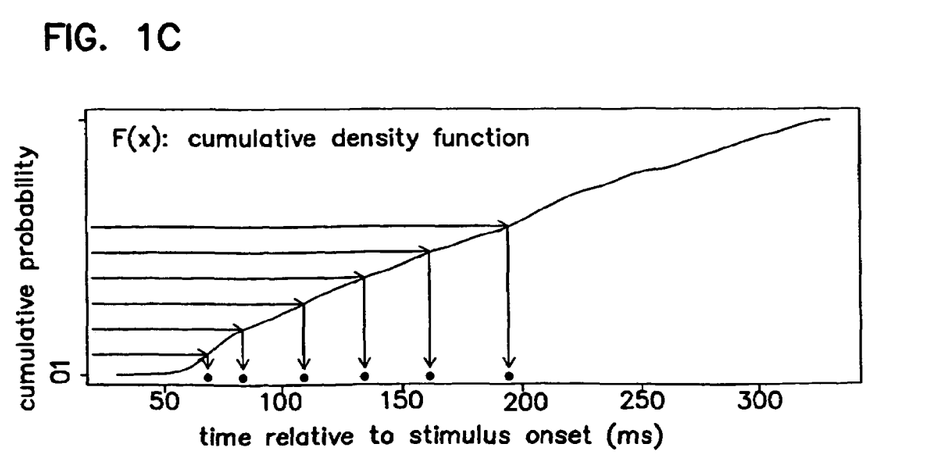
FIG. 1C is a graph representing the cumulative probability of a spike occurring at a certain time (msec) after onset of a stimulus, also referred to as the cumulative density function $F(x)$.

This model can be used to simulate spike trains that are indistinguishable from observed spike trains. Rasters of the responses of one V1 supragranular complex cell aligned at the time of stimulus onset are shown in FIG. 1A. The corresponding average spike density plot for those same responses are seen in FIG. 1B. The average spike density plot integrated over the whole period results in the curve seen in FIG. 1C. Such an integrated spike probability density function can then be used to generate the simulated spike trains using a uniform random number generator. The number of spikes needed is chosen from the number of spikes in the recorded data. In this example, six spikes were needed, so six random numbers would be chosen, placed on the ordinate and mapped through the cumulative spike density function as shown to generate the simulated spike train indicated by the dots at the bottom. Using this procedure places the spikes stochastically due to the random numbers. However, the probability density function averaged across many examples will be nearly indistinguishable from that in FIG. 1A.

By directly examining a sufficient number of simulated spike trains we can estimate what intended motor task caused the observed spike train. However, methods of the invention utilize closed-form calculations to determine the same information much more efficiently.

2. Spike Density Function

The second step of a method of the invention is to utilize the recorded spike trains to determine an overall spike density function for each stimulus.

One embodiment of a method of the invention calculates spike density functions by summing action potentials at each time bin to create a histogram. The histogram is then smoothed to calculate the spike density function. One method of determining the spike density function is to use a local regression with an adaptive bin width chosen using generalized cross validation. An example of a spike density function can be seen in FIG. 1B. The cumulative spike density function is calculated from the spike density function by summing the spike density function across time as shown in Equation 1 below.

$$F(t) = \Sigma_{t' \leq t} f(t') \qquad (1)$$

All of the order statistics depend on the spike density function, which must be estimated from data. The empirical firing rate histogram will typically have peaks and valleys reflecting actual variation in the firing rate over time as well as many small fluctuations due to random variation in the sample at hand. A preferred estimate of the spike density function would preserve the former while smoothing out the latter.

Histogram estimates are very sensitive not only to the bin width used, but also to the alignment of those bins. Kernel smoothing methods avoid the problems associated with bin alignment in histograms, but an inappropriate choice of kernel width (like an inappropriate choice of bin width) can lead to either under- or over-smoothing. Choosing the appropriate level of smoothing by eye, so the resulting fit "looks right", is not adequate. Instead, cross-validation is preferably used to ensure a statistically valid fit.

Cross-validation methods separate data into several subsets, using each to test the model fit on the others. Cross-validation is used for model selection in a variety of settings including a neuronal-network approach to estimating the information in neuronal responses. Leave-one-out cross-validation of a fit to a density selects a model based on some comparison of the density $d(t_i)$ measured at a point $t_i$ and the density $d_{-i}(t_i)$ predicted by the model estimated using all the points except $t_i$.

There are a variety of cross-validated fitting methods. Methods of the invention preferably use local polynomial fits to the empirical firing rate histogram, with the degree of smoothing determined by generalized cross-validation, based on least-squares methods. Local polynomial fits are calculated and selected using C Loader's LOCFIT software running under R.

For each neuron, spike density functions are calculated for each stimulus and for the entire set of responses together. Those stimuli that elicited fewer than five spikes cumulatively in response to all presentations of a particular stimulus were assigned the post-stimulus time histogram (PSTH) calculated for all stimuli together.

In another embodiment of the invention, the spike density functions are calculated by modeling the spike trains as a doubly stochastic Poisson process.

A doubly stochastic Poisson process is one way of modeling the occurrences of a sequence of discrete events. The defining characteristic of such a process is that the time intervals between successive events are exponentially distributed, and are treated as independent random variables drawn from an exponentially distributed population.

In doubly stochastic Poisson process, as used in methods of the invention, a firing rate is first chosen, and then events are generated using a Poisson process with the appropriate rate. Accordingly, the spike count distribution is modeled as a mixture of (preferably two to three) Poisson distributions. This reconceptulization reduces the amount of computation necessary to decode spike trains because for a Poisson process, some of the calculation can be done in closed form rather than computationally. Instead of treating each spike count individually, the distribution of first spike times for each of the component Poisson processes of the doubly stochastic Poisson process can be calculated.

Formally, consider the doubly stochastic Poisson process representing the trains elicited by some stimulus to be made up of component Poisson process with means $\mu_1, \ldots \mu_k$ for some k and weights $w_1, \ldots w_k$ such that $\Sigma_{i=1}^{k} w_i = 1$. Assume that the rate function for each subcomponent is simply a multiple of an underlying rate function $\lambda(t)$, where $$\int_{t_{start}}^{t_{finish}} \lambda(t) = 1.$$

For the ith subprocess, the probability of the first spike occurring between t and t+δt is shown in Equation 2 below.

$$p_i(t) = \exp\left(-\mu_i \int_{t_0}^{t} ds \lambda(s)\right) \left[1 - \exp\left(-\mu_i \int_{t_0}^{t_0+\delta t} ds \lambda(s)\right)\right] \qquad (2)$$

The distribution of the first spike times for the entire doubly stochastic Poisson process is simply the weighted sum of the subcomponent distributions, as given in Equation 3.

$$p(t) = \Sigma w_i p_i(t) \qquad (3)$$

Embodiments of the invention that model the spike count distribution using a non-parametrically or truncated Gaussian distribution require the distribution of first spike times for each spike count, where spike counts range from 0 to 30 (frequently) or even 70 (less frequently). However, this embodiment requires calculating the distribution of first spike times for only 1-5 Poisson subprocesses. As might be expected, this dramatically reduces computation time: in the current calculations, by a factor of 5-10.

Another advantage (both conceptual and computational) of this embodiment is that the distribution of spike counts can explicitly be calculated in any subinterval. If the doubly stochastic Poisson process is made up of subprocesses with mean rates (over the entire interval) $\mu_i \ldots \mu_k$ and weights $w_i \ldots w_k$, then the processes over a time subinterval from $t_0$ to $t_1$ is made up of subprocesses with mean rates $c\mu_1 \ldots c\mu_k$, where $$c = \int_{t_0}^{t_1} ds \lambda(s).$$

The conceptual advantage is that the predictions made by this model are borne out in the data, giving confidence in the model itself. The computational advantage is that because we can write down the Poisson process for any subinterval (and particularly, for the interval remaining), we no longer need to measure the spike count distribution for each subinterval, as was necessary in the other embodiment.

Overall, this embodiment of the invention, provides a complete model of the spike trains. This embodiment may be more parsimonious than the previous embodiment, because fewer parameters need to be measured directly from the data. This embodiment may also be computationally simpler than the previous embodiment.

3. Order Statistics

Order statistics describe the distribution of the k-th of n random numbers independently drawn from a single continuous distribution as illustrated in Equation 4.

$$h_{n,k}(t) = \binom{n}{k} F(t)^{k-1} f(t)[1 - F(t)]^{n-k} \quad (4)$$

where $f(t)$ is a density function, $F(t)$ is the corresponding cumulative density function, and $$\binom{n}{k},$$

used here as a normalizing factor, is shorthand for n!/[(n-k)!k!], a combinatorial expression for the number of ways to place k spikes in n bins. In the context of spike trains, $f(t)$ is the spike density function (FIG. 1B) and F(t) the corresponding cumulative spike density function. Thus to a first approximation, the (n, k) order statistic $h_{n,k}$ is the distribution of the k-th spike in a train with n spikes.

This formulation is not entirely appropriate for spike trains because it does not include a refractory period. A refractory period can be included by considering conditional order statistics as shown in Equation 5 below.

$$h_{n,k}(t \mid t_{k-1} = t') = \tilde{h}_{n-k,1}(t) = n - k)\tilde{F}(t)^0 \tilde{f}(t)\left[1 - \tilde{F}(t)\right]^{n-k-1} \quad (5)$$

where $\tilde{f}$ and $\tilde{F}$ are the conditional spike density function and cumulative spike density function given that the (k-1)-th spike occurs at time t'. In standard order statistics $\tilde{f}$ is calculated from the spike density function $f$ by left-truncating $f$ at t' and normalizing. Absolute and probabilistic refractory periods can be included in the definition of $\tilde{f}$ by multiplying the truncated version of $f$ by an appropriate time-dependent scaling factor g(t-t') before normalizing. The unconditional (n, k)-th order statistic is calculated by taking the appropriate weighted sum of conditional order statistics as shown in Equation 6.

$$h_{n,k}(t) = \sum_{t'} p(t_{k-1} = t') h_{n,k}(t \mid t_{k-1} = t') \quad (6)$$

This is a recursion equation: each (n, k) order statistic requires the previous (n, k-1) order statistic to evaluate $p(t_{k-1})$. The first order statistic is not conditioned on any previous spike, and so can be calculated using Equation 1.

Alternatively, the distribution of the k-th spike in all trains may want to be determined, not just those with a particular number of spikes. Such a distribution can be calculated by adding together the order statistics, weighted by the probability of observing different numbers of spikes as seen in Equation 7 below.

$$h_k(t) = \sum^n p(n) h_{n,k}(t) \quad (7)$$

4. Decoding a Spike Train

Methods of the invention determine the unknown stimulus that caused an observed spike train as follows.

Methods of the invention monitor spike trains elicited by known stimuli to calibrate or learn the functions and spike count distributions associated with each stimulus. From this, the methods calibrate the order statistics and count weighted order statistics. This information is then used to make the best estimate of the member of the set of unknown stimuli that elicited an observed response.

An important special case of the count weighted order statistic $h_k(t)$ is $h_1(t)$, which describes the probability of the first spike (or, using conditional order statistics as described above, the next spike after an observed spike) appearing at different times. To emphasize the fact that this probability function depends on which stimulus has been shown, we rename this function $h_{s,1}(t)$, adding a subscript denoting stimulus. The ensemble of functions $\{h_{s,1}(t)\}_{s \in S}$ gives the probability of the first spike occurring at different times for all stimuli s in the set S. The cumulative count weighted order statistic $H_{s,1}(t) = \Sigma_{t' \leq t} h_{s,1}(t)$ gives the probability of the first spike having occurred by some particular time, and $1 - H_{s,1}(t)$ gives the probability of the first spike arriving after time t. Given some prior distribution of stimulus probabilities, Bayes' Rule, as shown in Equation 8 below, calculates the new distribution of stimulus probabilities given an observed spike $$p(s \mid \text{next spike at time } t) = \frac{p(s) h_{s,1}(t)}{\Sigma_{s'} p(s') h_{s',1}(t)} \quad (8)$$

where p(s) is the estimated probability of stimulus s before seeing the spike at time t.

Equation 5 calculates the change caused by observing a spike in a downstream neuron's estimate of how likely each stimulus is to be the one that elicited the response under consideration. However, not seeing a spike at a particular time can also be informative, and the order statistic model can calculate the change in a neuron's estimate of stimulus probabilities at any time. The order statistic model makes it possible to calculate the change in stimulus probabilities from one time to the next as a spike either does or does not arrive. Because the count weighted order statistic $h_{s,1}$ gives the probability of a spike arriving at time t and not before, we require the conditional probability that a spike does or does not arrive at time t given that it did not arrive at time t-1. If a is the train up to time t-1 and b is the train up to time t, then the event a and b is the same as b, and the conditional probability of b given a is just p(b)/p(a). Thus the new information when the spike does or does not arrive at time t, given that it had not arrived by time t-1, is $h_{s,1}(t)/(1 - H_{s,1}(t-1))$ if a spike does arrive, and $(1 - H_{s,1}(t))/(1 - H_{s,1}(t-1))$ if a spike does not arrive. This leads to Equation 9 below.

$$p(s \mid \delta(t) \text{ and no spikes up to } t-1) = \frac{p(s)g_{s,1}(t)}{\sum_{s'} p(s')g_{s',1}(t) \mid s')} \quad (9)$$

where $$g_{s,1}(t) = \frac{h_{s,1}(t)}{1 - H_{s,1}(t-1)} \text{ if } \delta(t) = 1$$

$$g_{s,1}(t) = \frac{1 - H_{s,1}(t)}{1 - H_{s,1}(t-1)} \text{ if } \delta(t) = 0$$

It can be shown that calculating the changes in stimulus probability millisecond by millisecond until a spike occurs gives the same result as calculating the change in a single step using Equation 5.

5. Applying the Invention to Prosthetic Devices

While investigators record from neurons, the subject is asked to attempt (with the phantom limb) the various motions that the prosthetic will perform. A restricted set of motions is used, for example motion in only a few directions, or at only a single speed, could be investigated initially, with additional motions added later. The distribution of spike counts and spike density function associated with each motion can be estimated from the data collected. A few hundred repetitions of representative desired motions should suffice; furthermore, the adequacy of the estimate can be monitored while data is collected. Data collection can be stopped when the representation is sufficiently good or has stopped improving. Plugging the estimated parameters in to the model sets the decoder to estimate which desired motion generated a set of spike trains observed coming in from the recorded neurons. At set time intervals the decoder reports to the controller both its guess of the desired motion and its degree of certainty (based on the entire distribution of motion probabilities) that its guess is correct. The controller initiates the movement only when the certainty reaches some acceptable level. This prevents "runaway" prostheses from injuring the wearer or others. Increasing the number of neurons on which the decoder bases its guesses will reduce the time required to reach the desired level of certainty.

In one embodiment of a method of the invention, a single prosthesis is trained by monitoring neural data from an individual while predetermined movements are undertaken, and later utilized by the same individual. This method of training and utilizing a single prosthesis minimizes problems that may result from differences between different prosthesis, different users, and different neural probes.

Figure 2:
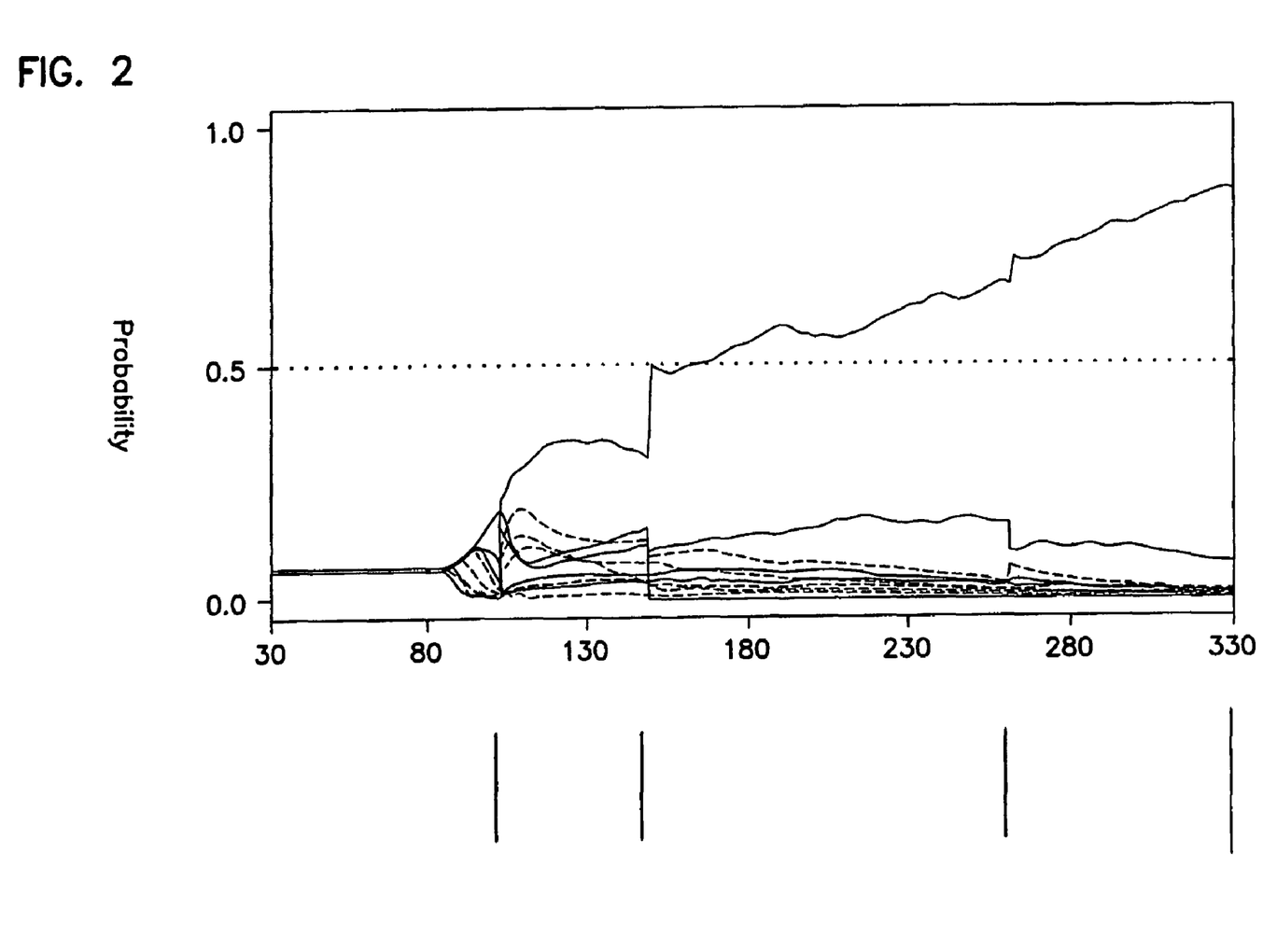
FIG. 2 is a graphical depiction of the probability of separate stimuli causing the observed spike train (represented by the marks under the x axis), also referred to as decoding the spike train.

FIG. 2 shows the results of applying the decoding procedure to a single train. The lines in the top panel show, for each of the 16 stimuli presented in the course of the experiment, the decoding procedure's estimate of the probability that that stimulus elicited the response. Each vertical bar at the bottom of FIG. 2 shows the time at which the neuron emitted an action potential. The x axis shows the time (in milliseconds) after stimulus onset. The y axis shows the probability with which each stimulus is believed to have elicited the response being decoded. Here, the neuron quickly estimates that the stimulus represented by the ascending line (which did in fact elicit this response) is most likely to have elicited this response.

Figure 3:
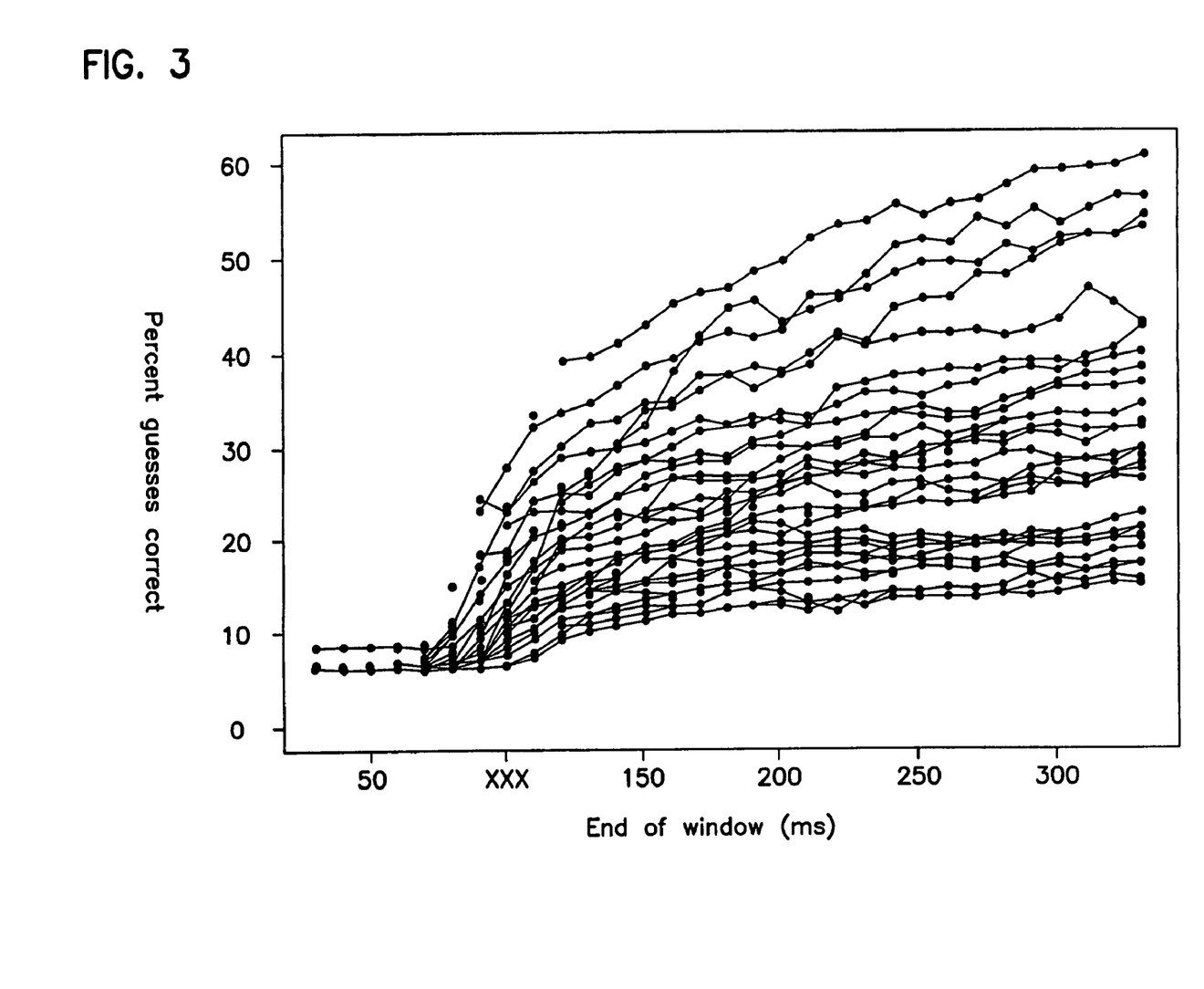
FIG. 3 is a graphical depiction of the accuracy with which single neurons decode the response over a fixed period of time.

If the decoding procedure always guesses that the highest-probability stimulus elicited the response, we can ask how accurate the decoding is. FIG. 3 shows the percent of trains decoded correctly by each of 29 neurons in monkey primary visual cortex. The x axis shows time from stimulus presentation in milliseconds. The y axis shows the percent of trials for which the response was actually elicited by the stimulus with the highest estimated probability. Results for 29 single neurons are shown. Accuracy increases with time. By the end of the 300 ms period examined, individual neurons accurately identify the stimulus that elicited a response between 15 and 60% of the time.

6. Methods of Implementing the Invention

One of skill in the art, having read this specification, would know how to incorporate a method of the invention into a system comprising a prosthetic limb. Examples of specific embodiments of such incorporation are explained in more detail below.

The method and device of the invention can be used with virtually any prosthetic that is capable of or can be modified to be capable of being instructed to carry out motor tasks. The method and device of the invention can be used with any type of prosthetic limb, including for example arms and legs. More preferably, the method and device of the invention is used with prosthetic arms.

The method of the invention can be incorporated into any device capable of electronically storing the information, practicing the invention, or combinations thereof. Preferably, the method of the invention is incorporated into an electronic media storage device which is coupled with a computer processor, a neural probe, and a power source. Such an embodiment of the invention is preferably configured so that the neural probe is in electrical contact with the wearer's limb, the neural probe is also electrically coupled to the microprocessor, the microprocessor is electrically coupled to the actuators of the prosthetic limb so that the limb can carry out actions as directed by the microprocessor. In such an embodiment, the power source can be coupled to individual components that need power, or can be coupled in series.

The computer processor is typically an embedded processing system capable of being housed within the device and operated using a power storage device, such as a battery. The processing system itself may be a general purpose processing system, as is known to those of skill in the art. This embodiment of a device of the invention may include an electronic media storage device and/or a computer processor.

Microprocessors for use with devices incorporating methods of the invention can be chosen from those that are normally used by those of skill in the art. In one embodiment, the microprocessor can be coupled to a read-only-memory (ROM) and a random-access-memory (RAM). In such an embodiment, the ROM can contain the instructions for carrying out the method of the invention. In this embodiment, the results of a decoded neural signal are temporarily stored in the RAM.

Neural probes for use with devices incorporating methods of the invention can be chosen from those that are normally used by those of skill in the art. Preferably, such devices utilize microelectrodes. A specific, and preferred example of such a microelectrode is a tungsten microelectrode with an impedance of 0.8-1.3 MΩ (MicroProbe, Clarksburg Md.). The microelectrode is preferably housed in a stainless steel guide tube so that the dura could be penetrated.

Power sources for use with devices incorporating methods of the invention can be chosen from those that are normally used by those of skill in the art. In one embodiment, one power source provides the requisite power to all components that need power, such as the microprocessor and the actuators of the prosthetic limb. In another embodiment, the separate components can be controlled by separate power sources. Power sources can include batteries such as rechargeable or disposable batteries.

While the above embodiments of the invention describe the use of a decoding algorithm of neuronal responses for use in generating instructions to a mechanical prosthesis, one skilled in the are will recognize that the use of the processing system discussed above are merely example embodiments of the invention. As long as physiological data is used to provide the necessary instructions, the present invention to would be useable in other data processing systems. It is to be understood that other embodiments may be utilized and operational changes may be made without departing from the scope of the present invention as recited in the attached claims.

WORKING EXAMPLES

Example 1

Recording a Spike Train

Action potentials from neurons were monitored in the visual cortex of monkeys. The data was monitored with a tungsten microelectrode with an impedance of 0.8-1.3 MΩ (MicroProbe, Calrksburg Md.). The microelectrode was housed in a stainless steel guide tube so that the dura could be penetrated. A hydraulic microdrive was mounted on the recording cylinder. Experimental control and data collection were performed by a Hewlett Packard Vectra 486/33, using a real time data acquisition system adapted for the QNX operating system. Single units were discriminated according to spike shape and amplitude by calculating principal components.

Figure 4:
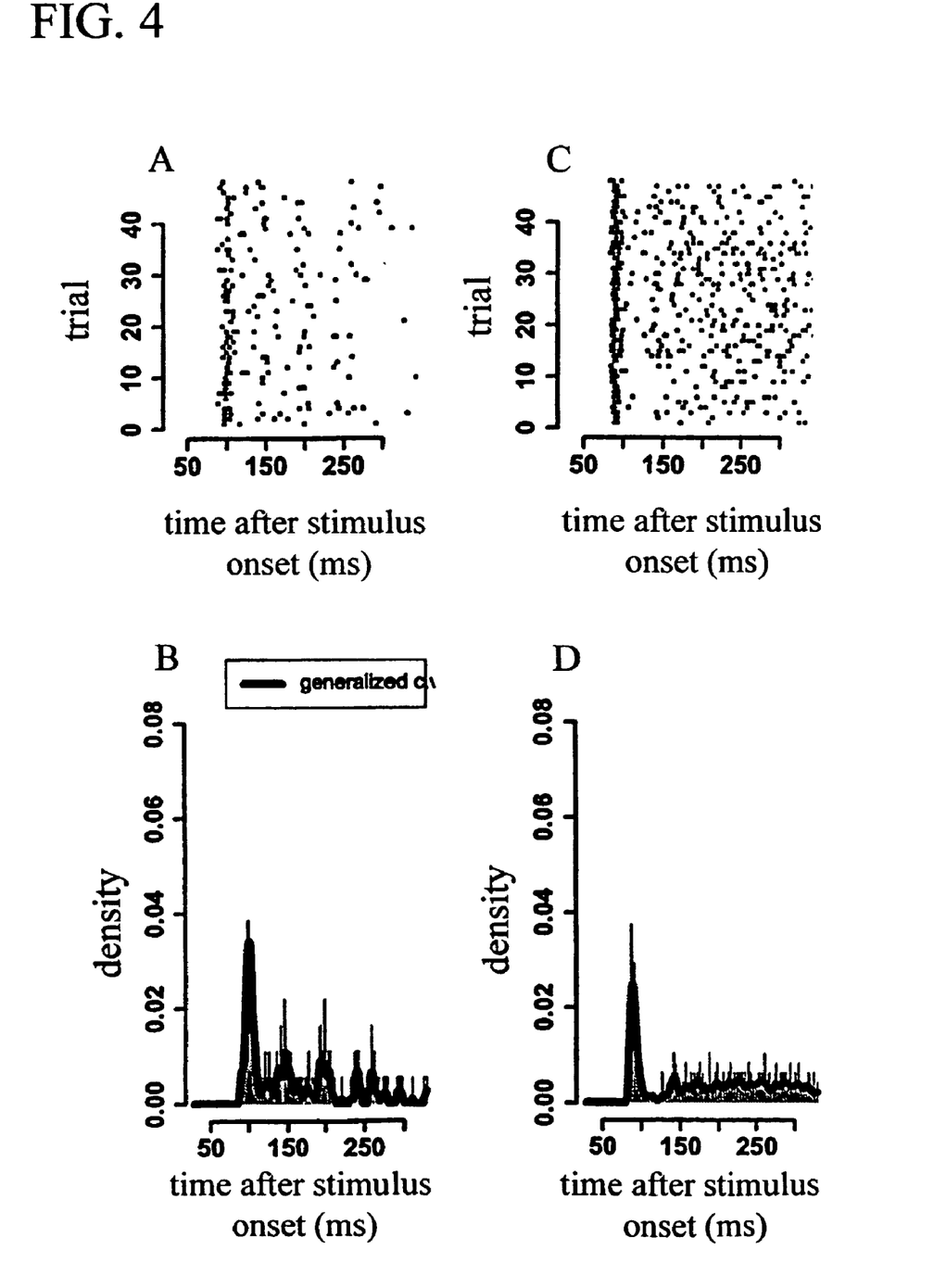

FIGS. 4A, C, E, and G show responses elicited from a single neuron by four different stimuli. The responses are represented by dot diagrams (rasters). In each FIGS. (6A, C, E, and G) each horizontal row of dots represents a separate presentation of the stimulus to the neuron. Each dot in any row marks the time of occurrence of an action potential after the presentation of the stimulus (0 msec is the point at which the stimulus was presented to the neuron).

Example 2

Determining Spike Density Function

FIGS. 4B, D, F, and H show the corresponding spike density functions for the raw data recorded above. The gray histograms sum the data of FIGS. 4A, C, E, and G across the trials to show the probability of spikes occurring in each 1 ms bin. The spike density functions, the lines in FIGS. 4B, D, F, and H are then calculated from the histograms by creating a smoothed version of the histogram. Spike density functions were fit using local regression, with adaptive bin width chosen using generalized cross validation. Note that both histograms and spike density functions sum to 1, so the number of spikes in each trial is not represented in these panels. The cumulative spike density functions are obtained by adding up the spike density functions over time, See equation 1.

Example 3

Determining the Cumulative Spike Density Functions

Figure 5A:
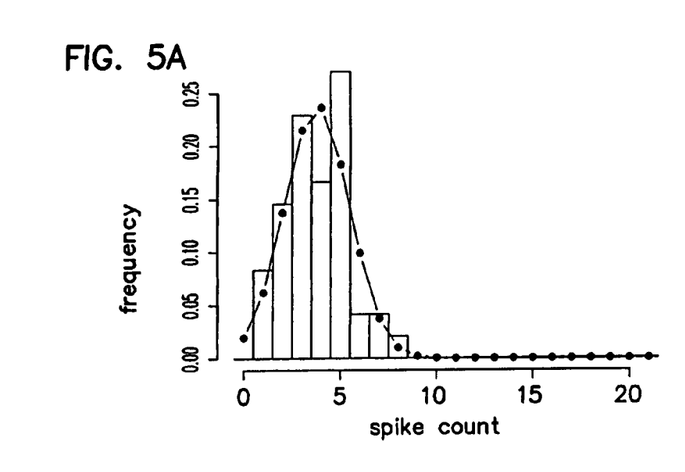
FIGS. 5A, B, C, and D depict the cumulative spike density functions of the spike trains depicted in FIGS. 4A, C, E, and G.
Figure 5B:
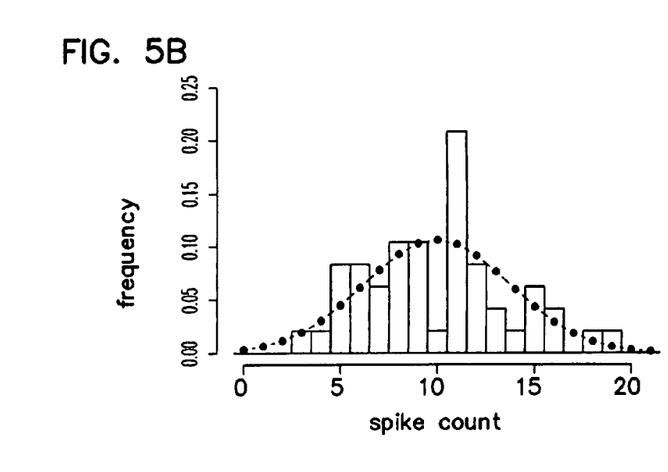
Figure 5C:
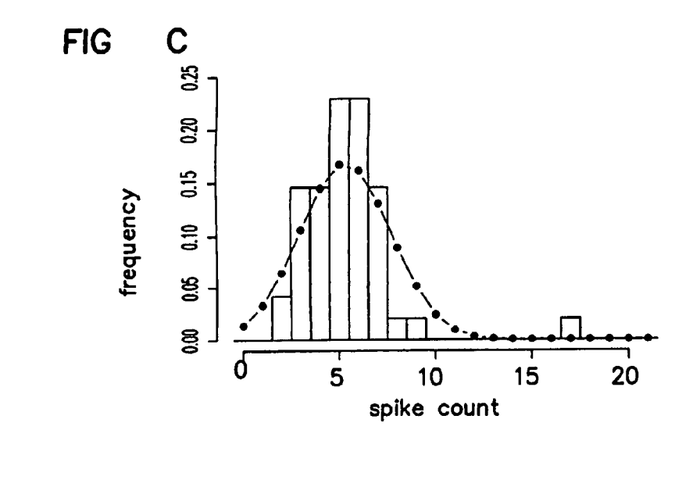
Figure 5D:
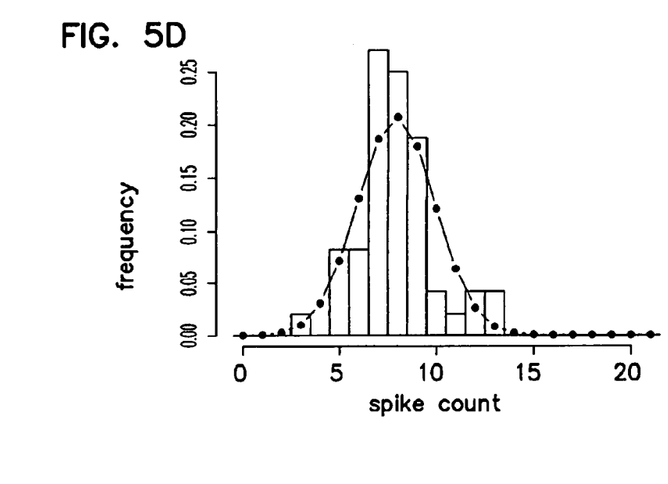
Figure 6A:
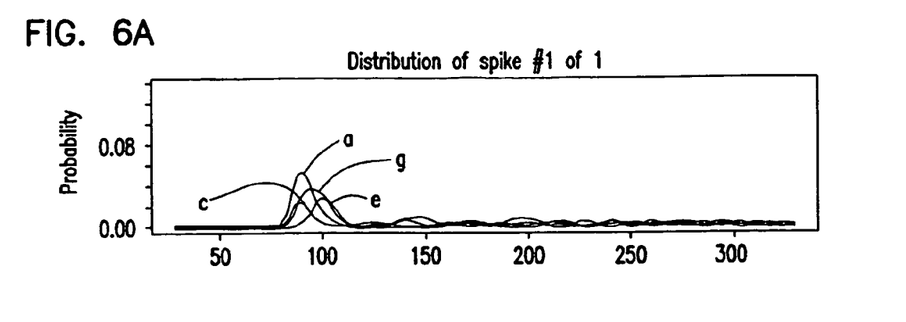
FIGS. 6A, B, C, and D depict the first order statistics for the data from the four stimuli shown in FIG. 4 in spike trains with 1 (A), 2 (B), 5 (C), and 10 (D) spikes respectively. The x axis shows time (msec) after stimulus presentation and the y axis shows the probability of the first spike occurring at each time.
Figure 6B:
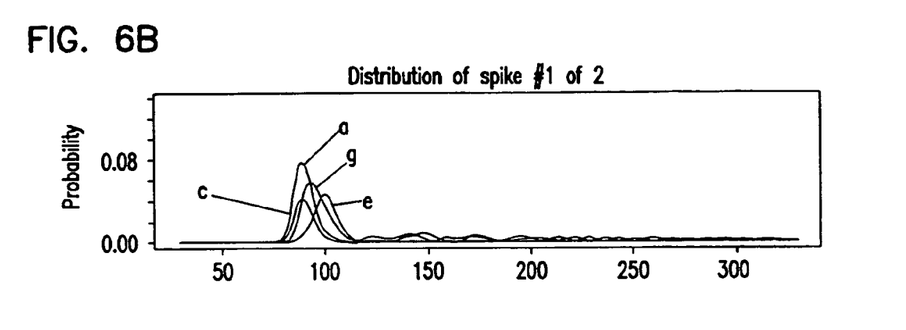
Figure 6C:
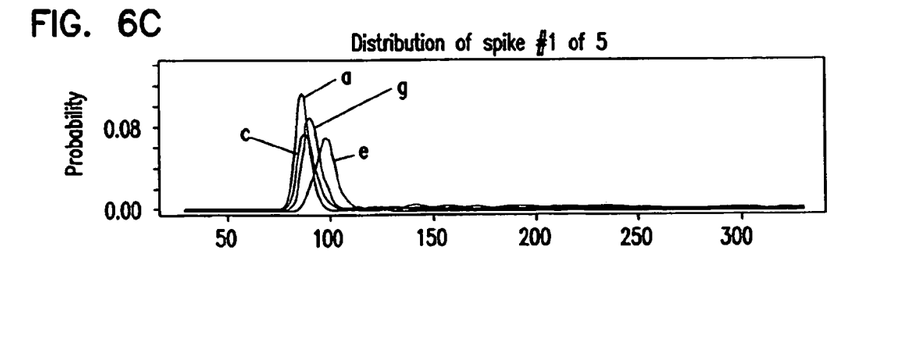
Figure 6D:
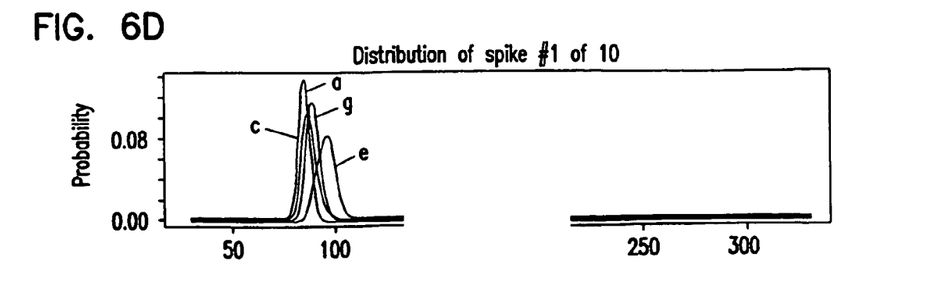

FIGS. 5A, B, C, and D show the cumulative spike density functions for the four stimuli. The histograms show the observed count distributions; the curves show a truncated Gaussian approximation to each distribution. Truncated Gaussian distributions have been shown to be a good approximation to count distributions in several areas of the brain, and are utilized in one embodiment of the invention to determine the cumulative density function.

Example 4

Calculation of the Order Statistics for the Stimuli

Once the cumulative spike density functions have been determined from the raw data, the order statistics can be computed. As explained above, order statistics describe the distribution of the k-th of n random numbers independently drawn from a single continuous distribution:

$$h_{n,k}(t) = \binom{n}{k} F(t)^{k-1} f(t)[1 - F(t)]^{n-k} \tag{4}$$

where $f(t)$ is a density function (calculated in FIGS. 4B, D, F, and H) and F(t) is the corresponding cumulative density function (shown in FIGS. 5A, B, C, and D). FIG. 6 shows the first order statistics for the data from the four stimuli (the stimuli associated with the spike trains from FIGS. 4A, C, E, and G are designated a, c, e, and g respectively) shown in FIG. 6 in trains with 1, 2, 5, and 10 spikes. In each panel the x axis shows the time after stimulus presentation, and the y axis shows the probability of the first spike occurring at each time. Note that the actual distribution of counts elicited by a stimulus does not need to be known to calculate the order statistics.

A neuron receiving a spike train does not know how many spikes will be in the train. Therefore for decoding it is desirable to know the distribution of (in our example) the first spike overall. This distribution is given by the count weighted order statistics, obtained by adding together the order statistics weighted by the probability of observing different numbers of spikes:

$$h_k(t) = \Sigma p(n) h_{n,k}(t) \tag{7}$$

Figure 7:
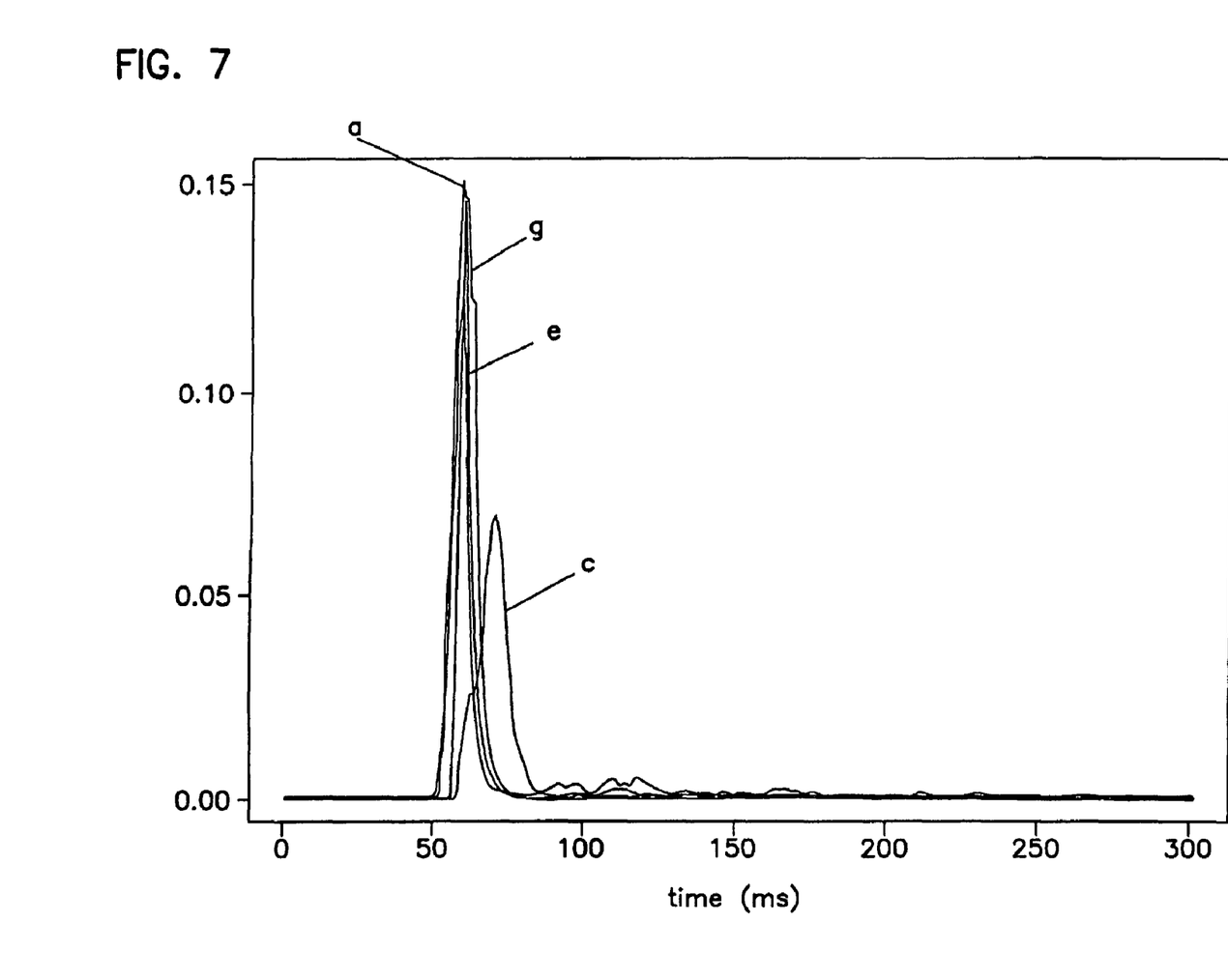
FIG. 7 depicts the count weighted first order statistics for the four stimuli monitored in FIGS. 4A, C, E, and G. The x axis shows the time (msec) after the stimulus was presented, and the y axis shows the probability of the first spike occurring at each time.

A nominal bin accounts for spikes occurring beyond the observation window, that is, for trials with zero spikes. Thus the count weighted first order statistic for a stimulus will not integrate to one over the observation window if there is a non-zero probability that that stimulus elicits no spikes. FIG. 7 shows the count weighted first order statistics for the four stimuli (a, c, e, and g). The x axis shows the time after stimulus presentation, and the y axis shows the probability of the first spike occurring at each time. The distributions sum to 0.96, 1, 0.99, and 1 That is, the probability of observing 0 spikes for the four stimuli is 0.04, 0, 0.01, and 0 (compare FIG. 6).

Example 5

Decoding a Spike Train

Figure 8:
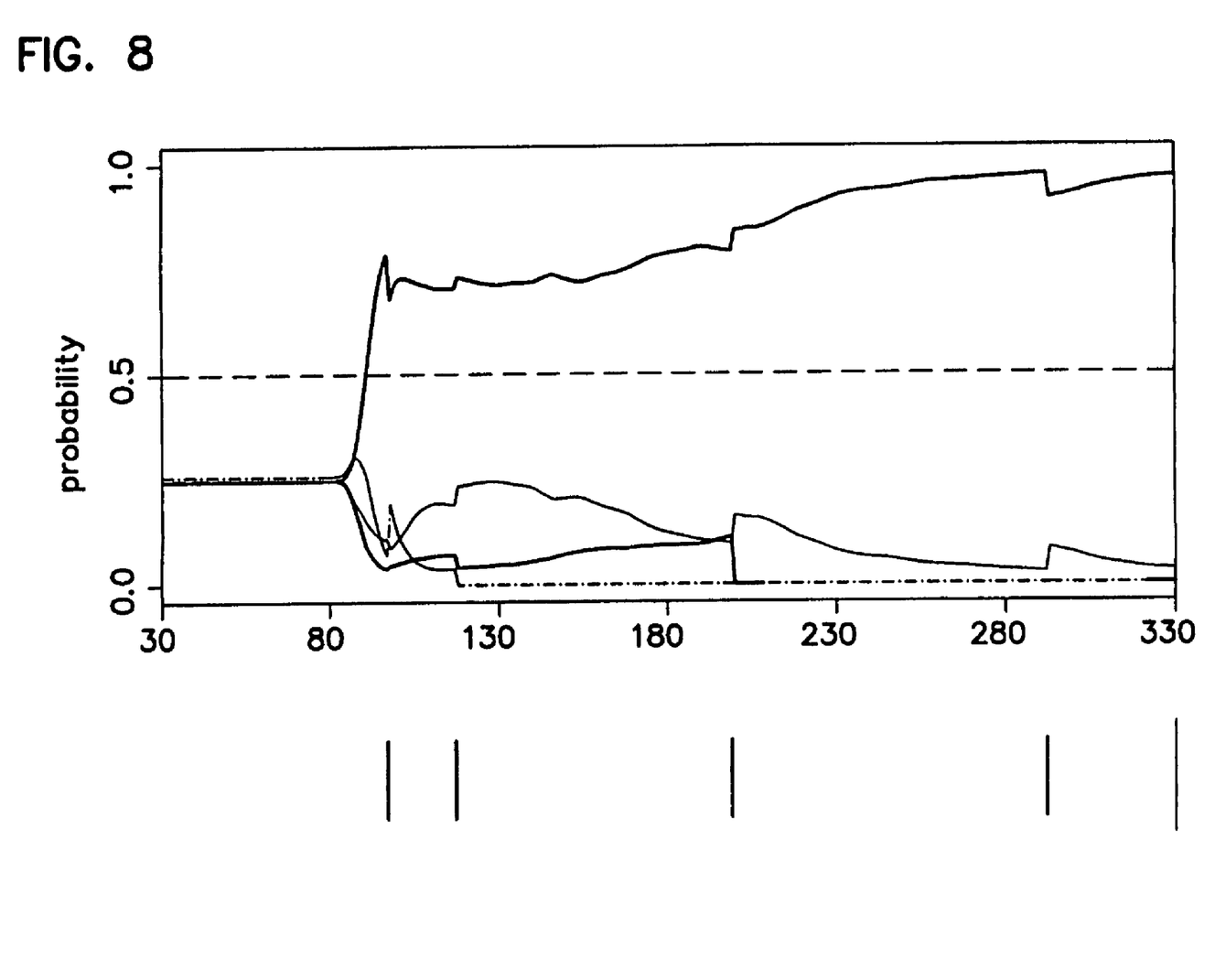
FIG. 8 represents the decoding of a spike train elicited by the black stimulus, the actual spike train is depicted by the hatch marks below the x axis. The lines represent the probabilities of the spike train being caused by the black, red, green and blue stimuli.

The first spike times for the stimulus represented by the black line (a) tend to be later than those for the other stimuli (FIG. 7). The effect of this is seen when the neuron decodes a spike train elicited by the black stimulus (a). The first spike in the train occurs 97 ms after stimulus onset, as seen in FIG. 8. The x axis shows time from stimulus onset; they axis shows the estimated probability that the spike train shown at bottom was elicited by each stimulus (a, c, e, and g). When more than 90 ms have passed since stimulus onset, the decoding algorithm detects that a first spike must now be relatively late, so the black stimulus (a) is more likely. The arrival of the first spike 97 ms after stimulus onset actually makes the black stimulus (a) somewhat less favored (first dip in the black curve (a), with corresponding rise in the blue curve (g)).

Further count weighted order statistics conditioned on the observed spikes were calculated. Each time a spike is observed, new order statistics are calculated from the truncated spike density functions and weighted using the distribution of counts expected in the remaining time. The results of the rest of the decoding can be seen in FIG. 8. Note that the probabilities at any time are based only on the response up to that time. No knowledge of how many additional spikes will arrive is available to the decoding algorithm.

Example 6

Validating the Decoding

Figure 9:
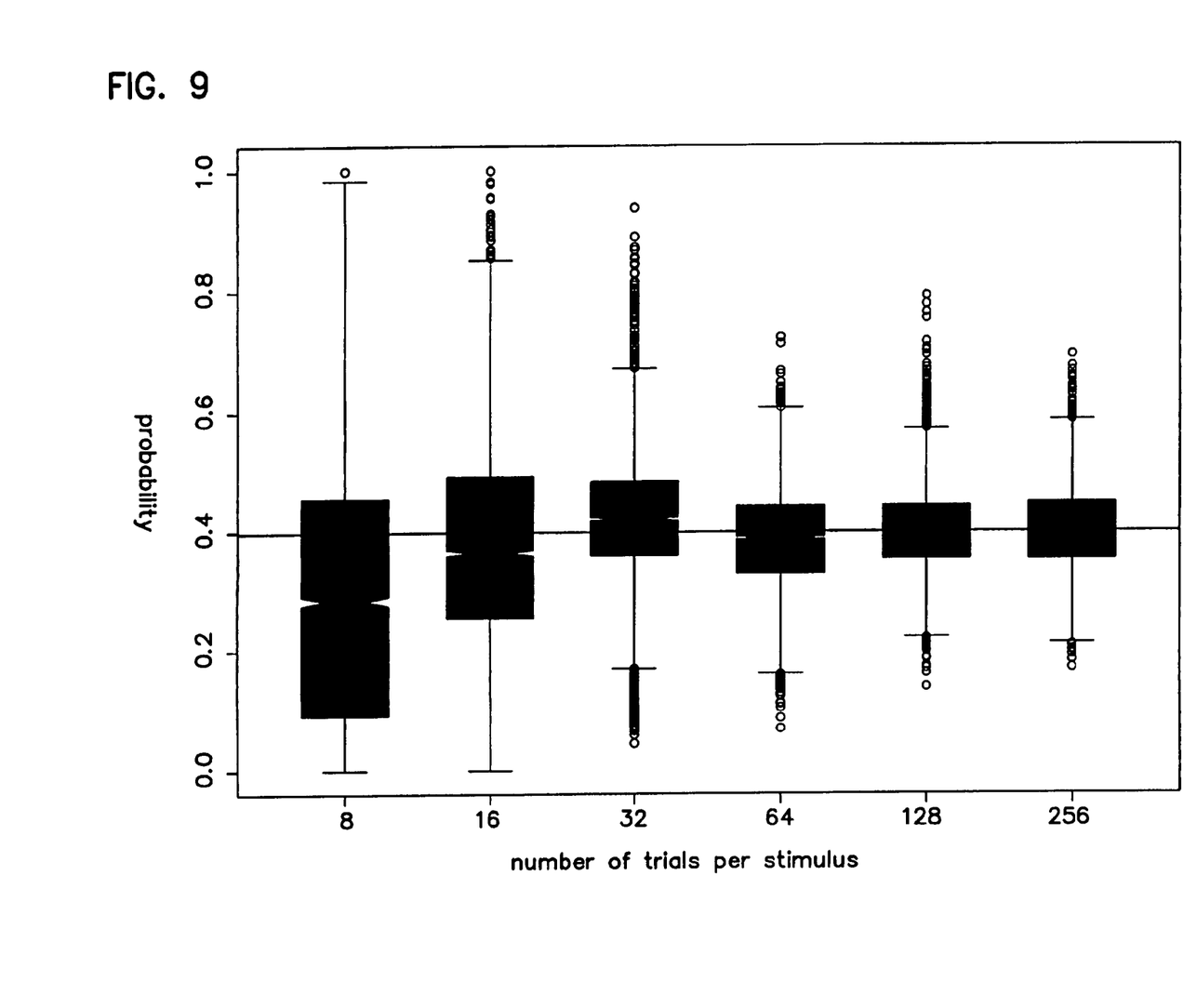
FIG. 9 represents the probabilities that the stimulus estimated by a method of the invention is correct with an increasing number of trials per stimulus.

As a basic check on the decoding algorithm, we created two situations in which the proper outcome is known. First we created artificial data sets with equal numbers of trials for two artificial stimuli. The PSTHs used for the two stimuli were identical, and the data were generated according to the spike count matched model (described in our earlier notes), so spike timing carried no unique information distinguishing responses to the two artificial stimuli from one another. All information that could be used to distinguish responses to the two stimuli was contained in the spike count distributions. In this situation Bayes' Rule shows that the probability with which an observed response made up of n spikes was elicited by a particular stimulus (as opposed to all other stimuli) is proportional to the probability with which each stimulus elicits responses with n spikes (as opposed to responses with other numbers of spikes). In this case we compared two artificial stimuli that elicited Poisson distributions of spike counts with means of 4 and 10, respectively, with flat spike density functions. A set of 500 randomly generated test spike trains with 7 spikes per train was decoded using the order statistic method. With increasing numbers of trials per stimulus the stimulus probabilities estimated by the order statistic model converge to the probabilities expected based on the spike count distributions (approximately a 40% chance of belonging to stimulus eliciting counts with a mean of 4; FIG. 9). It can be shown analytically that if a stimulus elicits no spikes, the order statistic model gives exactly the probabilities expected based on spike count.

Figure 10A:
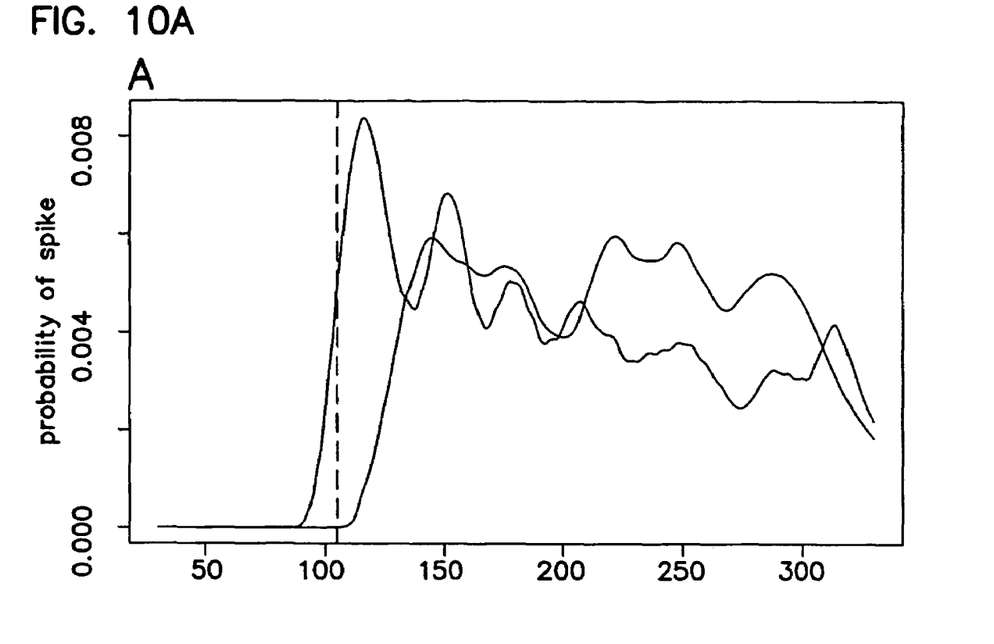
FIG. 10A represents the probabilities, estimated by a method of the invention, that a certain stimulus would cause a spike to occur at any given time.
Figure 10B:
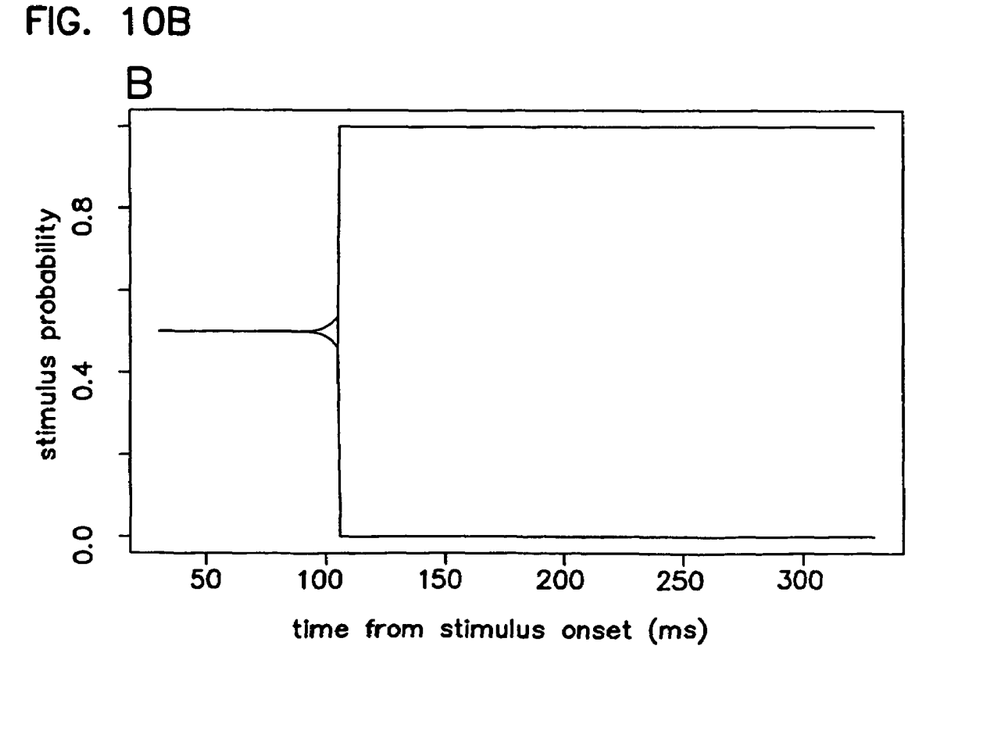
FIG. 10B represents the probability, as a function of spike onset, that one of two stimuli caused the spike train.

At the other end of the spectrum are situations in which all of the information about which stimulus elicited a response is available from spike timing. This occurs, for example, when some range of spike times can be elicited by only one of the stimuli (FIG. 10A). When a spike occurs at one of the stimulus-specific times, the model correctly determines that only one stimulus could have elicited the observed response (FIG. 10B).

The above specification, examples and data provide a complete description of the manufacture and use of the composition of the invention. Since many embodiments of the invention can be made without departing from the spirit and scope of the invention, the invention resides in the claims hereinafter appended.

The claimed invention is:

1. A prosthetic device comprising:
    a) a prosthetic limb;
    b) a recording device for recording action potentials from a neuron;
    c) a device comprising an input device for receiving and monitoring recorded action potentials from the recording device, a processor encoded with instructions for determining a spike density function from the recorded action potentials over time and an algorithm that computes a count weighted order statistic to determine the probability that the spike density function relates to a requested motor task, and a controller for initiating stimulation of the requested motor task; and
    d) a stimulation device for making said prosthetic limb carry out the requested motor task.

2. The prosthetic device of claim 1 wherein the device comprises an electronic media storage device.

3. The device of claim 1 wherein the recording device for recording action potentials from a neuron is a microelectrode.

4. The device of claim 3 wherein the microelectrode is a tungsten microelectrode.

5. The device of claim 3 wherein the microelectrode records in a range of from about 0.8 to 1.3 mega ohms.

6. The prosthetic device of claim 1, further comprising a memory for storing the decoded neural signal.

7. The prosthetic device of claim 1, wherein the algorithm that determines the probability that the spike density function relates to a requested motor task comprises a count weighted order statistic of spike density functions obtained from recorded action potentials generated by a known motor task.

8. The prosthetic device of claim 1, wherein the processor further encodes instructions for carrying out a method to determine the probability that a spike density function relates to a requested motor task and the certainty of the probability comprising determining a spike density function by determining the frequency of action potentials per millisecond from the occurrence of the initial stimuli for one or more motor tasks and statistically describing the distribution of the action potentials in said spike function for each motor task, and generating a probability function that allows classification of the spike density function to a requested motor task.

* * * * *